United States Patent [19]
Krueger

[11] Patent Number: 6,095,816
[45] Date of Patent: Aug. 1, 2000

[54] DENTAL IMPLANT COMPONENT HOLDER

[75] Inventor: Kenneth K. Krueger, Laguna Niguel, Calif.

[73] Assignee: Nobel Biocare USA, Inc., Yorba Linda, Calif.

[21] Appl. No.: 08/932,159

[22] Filed: Sep. 17, 1997

[51] Int. Cl.[7] .................................................. A61C 3/00
[52] U.S. Cl. .................................................. 433/163; 433/173
[58] Field of Search ........................... 433/50, 141, 172, 433/173, 163

[56] References Cited

U.S. PATENT DOCUMENTS

| | | | |
|---|---|---|---|
| 3,393,451 | 7/1968 | Rasch | 433/141 |
| 5,129,823 | 7/1992 | Hughes | 433/173 |
| 5,133,662 | 7/1992 | Metcalfe | 433/172 |
| 5,249,962 | 10/1993 | Ascher | 433/141 |
| 5,290,171 | 3/1994 | Daftary et al. | 433/141 |

*Primary Examiner*—John J. Wilson
*Attorney, Agent, or Firm*—Knobbe, Martens, Olson & Bear LLP

[57] ABSTRACT

A dental implant component package and holder for permitting the user, a dentist or oral surgeon, to readily remove the component from a sterile package is disclosed.

2 Claims, 1 Drawing Sheet

DENTAL IMPLANT COMPONENT HOLDER

FIELD OF THE INVENTION

This invention relates to dental implant technology

BACKGROUND OF THE INVENTION

Dental implant technology is well developed and there is a large body of literature describing this technology in technical reports, professional literature and patents. Indeed, within the past decade, this has become a very crowded art.

The prior art discloses a vast array of dental implant components. For convenience, the term "implant components" or simply "components" will be used herein as a shorthand reference to all of the components of a dental restoration or other procedure that involves the implantation of a pin, screw or other device into the jaw of a patient, including the components attached thereto, such as abutments, copings, prostheses and attaching components such as screws, pins, washers, etc. The reader is referred to the following U.S. Patents to illustrate, in general, a few of the types of components that may be used U.S. Pat. No. 5,476,382 to Daftary, U.S. Pat. No. 5,431,576 to Daftarv, U.S. Pat. No. 5,431,567 to Daftarv, U.S. Pat. No. 5,030,096 to Hurson, et al., and U.S. Pat. No. 4,856,648 to Krueger.

The components used in dental implant technology are very small, so small, indeed, that in many instances it is impossible visually to distinguish between different sizes, and sometime it is difficult to distinguish even between different components. Magnification and/or the use of calipers or other measuring devices are often necessary to ascertain exactly the type and size of the component.

A great variety of types and sizes of components must be kept on hand to assure that the dentist or oral surgeon has the right type of component in the right size to treat a patient. Sometimes, a preliminary procedure or examination enables the doctor to determine in advance the type and size of a dental implant, abutment, coping, etc., that will be required; however, a change of type or size may be required while a procedure is being carried out as a result of the discovery of a problem not previously known, or some other circumstance which cannot be fully determined until the procedure begins. Often, Of course, the type or size of a dental implant component is unknown or cannot be determined until a dental or surgical procedure is begun. In all cases, however, it is important that the doctor have on hand a substantial number of components to assure that the proper components are on hand.

Dental implant components, being very small, are difficult to handle. Many are so small that extremely well developed manual dexterity is required simply to hold them in a given position and special holding tools are required to use them.

Efforts have been made to provide packaging and holders to enable the doctor to identify, select and/or to hold the component and to use the component in a dental or surgical procedure, U.S. Pat. No. 4,856,648 to Krueger, U.S. Pat. No. 5,290,171 to Daftary and U.S. Pat. No. 5,030,096 to Hurson, et. al., are exemplary of such efforts.

A companion problem is that of maintaining sterility of the dental implant component. Such components are frequently pre-sterilized by the manufacturer in a sealed package or envelope. Sterility is reliably obtained and reasonably assured so long as the sterile package is not opened or damaged. The dentist often finds it difficult to handle these small components and yet maintain sterility. The component must be removed from the sterile package and transferred to the opening in the patient's mandible or maxilla directly or by way of a sterile surgical holder or instrument. Removing the small component from the package while maintaining sterility is a serious inconvenience. Facets of this problem, and examples of the types of components of concern, are addressed in the following U.S. Pat. No. 4,976,617 to Carchidi; U.S. Pat. No. 4,941,227 to Sussman, U.S. Pat. No. 5,062,800 to Niznick, U.S. Pat. No. 5,290,171 to Daftary, et. al., U.S. Pat. No. 5,368,160 to Leuschen, et. al., U.S. Pat. No. 5,538,428 to Staubli, U.S. Pat. No. 5,558,230 to Fischer, et. al.; and U.S. Pat. No. 5,582,299 to Lazzara et. al, One facet of the present invention addresses this problem.

Notwithstanding the many efforts in this crowded art to provide the doctor with dental implants and dental prostheses and components thereof in a way that will permit quick and certain identification and provide means for handling dental implant components, there remains the need for a compact orderly system and apparatus to minimized space requirements in the doctor's operating room and, at the same time, present the components in a convenient manner for identification, handling, and use. This invention meets this need more efficiently and more conveniently that any system or apparatus of which the inventors are aware.

SUMMARY OF THE INVENTION

The present invention is embodied in a component attached to a special holder for the component. The holder is an elongate member having a length and proximal and distal ends, a width and a thickness, the width being greater than about ten times the thickness, the length being from about three-fourths inch to one inch and being greater than about four times the width. The holder is constructed and configured to define a generally circular component holding aperture through the thickness thereof adjacent the proximal end and a V-shaped entry communicating with the aperture and extending to the proximal end of the holder.

DESCRIPTION OF THE PREFERRED EMBODIMENTS

Figure 1:
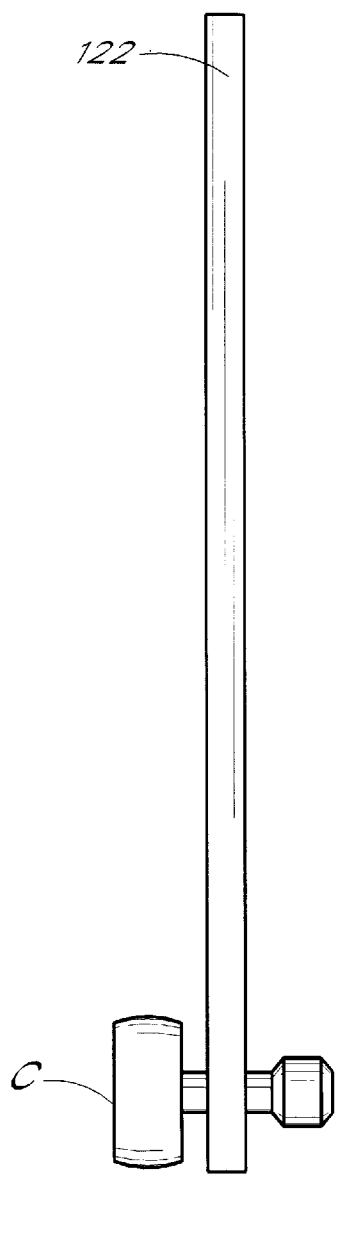
FIG. 1 is a side view of the component holder of this invention holding an exemplary component, an implant screw

The following description and the exemplary embodiments depicted in the drawings disclose the best form of the invention presently known to the inventors. Neither the description nor the drawings are, however, limiting. There are many facets to the invention. The invention can be made of a combination of any of a large number of materials. The configuration of each of the individual components may vary considerably, so long as the relationship permits display and use. Indeed, many variations and adaptations can be made within the spirit of the invention and without departing from the claims. Thus, the specification and drawings are exemplary, not limiting.

In one preferred form of the invention, the component is contained in an individual component box described in copending application Ser. No. 08/932,160 filed Sep. 17, 1997, now U.S. Pat. No. 5,967,305 entitled DENTAL IMPLANT COMPONENT PACKAGE AND HOLDER, wherein the present inventor is a co-inventor. However, the invention may be used in association with any containment system.

Figure 2:
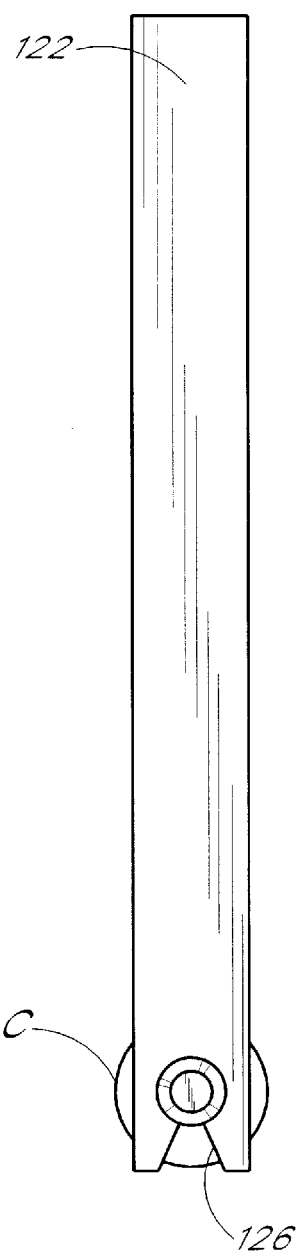
FIG. 2 is a front view of the component holder of this invention, as shown in FIG. 2, showing an implant screw mounted thereto The back of the holder is a mirror image of the front.
Figure 3:
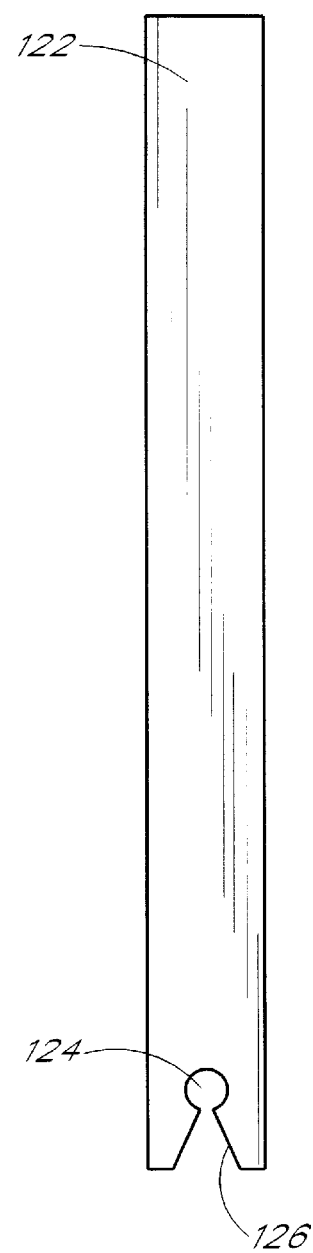
FIG. 3 is a front view of the component holder of this invention, as shown in FIG. 1, without a component mounted thereto. The back of the holder is a mirror image of the front.

The component C is held by a holder 122. A side view of the holder 122, as shown in FIG. 1, depicts the holder attached to the component C, an implant screw being the exemplary dental implant component. The front view of the holder 122 shown in FIG. 2 attached to the component C and the front view without the component depict the elegantly simple grasping structure of the holder The holder is constructed of a resilient, semirigid polymer and configured to define an aperture 124 for receiving a dental implant or prosthesis or a component thereof, e.g., the exemplary dental implant screw C, and an entry structure 126 which is of a size and shape to permit the implant, prosthesis or component thereof to be inserted into the aperture 124 against the resilient bias of the material of the holder 122. The component holder is attached to and extends from the component. The holder is constructed of a resilient, semi-rigid polymer configured to define an aperture for resiliently receiving and hold the component. The holder also defines entry structure communicating with the aperture constructed and configured to permit the component to be inserted into the aperture against the resilient bias of the holder material. The material is rigid enough to enable the user, e.g., a dentist or oral surgeon, to grasp the distal end thereof, shown at the top in the FIGS., with sterile gloved fingers, forceps or another grasping tool to move the component to a desired location for implantation or association with other components. The material of which the holder 122 is made is also resilient enough that the component is grasped by such resilience in the aperture 124.

In the preferred form, the holder is an elongate member having a length and proximal and distal ends, a width and a thickness, the width being greater than about ten times the thickness, the length being from about three-fourth inch to one inch and being greater than about four times the width. The holder is constructed and configured to define a generally circular component holding aperture through the thickness thereof adjacent the proximal end and a V-shaped entry communicating with the aperture and extending to the proximal end of the holder.

Polymers such as nylon, polyacetal, polystyrene, polycarbonate, and many other polymers are readily formulated using known techniques to have the required rigidity and resilience.

It will be apparent from a review of the foregoing that a convenient system is provided which provides for compact storage, convenient display, ready and safe access and convenient sterile handling has been provided.

INDUSTRIAL APPLICATION

This invention is useful in dentistry and in the dental implant industry.

What is claimed is:

1. A dental implant component holder for making a dental implant or prosthesis component conveniently usable by a dentist or oral surgeon comprising, in combination: the component held in an elongate holder that is constructed of a resilient, semi-rigid polymer constructed and configured to define an elongate strip having a thickness, and width of at least about ten times the thickness, and a length of at least about three fourths inch and at least about four times the width, proximal and distal ends and structure defining proximate one end thereof an aperture for resiliently receiving and holding the component and generally V-shaped entry structure intersecting said aperture constructed and configured to permit the component to be inserted into the aperture against the resilient bias of the holder material and to permit the user to position the component by grasping the other end of the holder.

2. A dental implant component holder for making a dental implant or prosthesis component conveniently usable by a dentist or oral surgeon comprising, in combination: dental implant component held in a holder that is configured and constructed to define an elongate member having a length and proximal and distal ends, a width and a thickness, the width being greater than about ten times the thickness, the length being from about three-fourth inch to one inch and being greater than about four times the width, the holder being constructed and configured to define a generally circular component holding aperture through the thickness thereof adjacent the proximal end and a V-shaped entry communicating with the aperture and extending to the proximal end of the holder.

* * * * *